United States Patent
Bainczyk et al.

(10) Patent No.: US 8,283,175 B2
(45) Date of Patent: Oct. 9, 2012

(54) TEST DEVICE FOR DETERMINING AN ANALYTE CONCENTRATION

(75) Inventors: Gregor Bainczyk, Mannheim (DE); Thomas Eisele, Mannheim (DE); Herbert Wieder, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 586 days.

(21) Appl. No.: 11/963,155

(22) Filed: Dec. 21, 2007

(65) Prior Publication Data

US 2009/0098018 A1    Apr. 16, 2009

Related U.S. Application Data

(63) Continuation of application No. PCT/EP2006/063208, filed on Jun. 14, 2006.

(30) Foreign Application Priority Data

Jun. 22, 2005   (EP) ...................... 05013396

(51) Int. Cl.
*G01N 35/00* (2006.01)
*G01N 33/49* (2006.01)

(52) U.S. Cl. ............... 436/46; 436/43; 436/45; 436/95; 422/63; 422/64; 422/68.1; 422/82.01

(58) Field of Classification Search .............. 436/45, 436/46, 43, 95; 422/63, 64, 68.1, 82.01
See application file for complete search history.

(56) References Cited

U.S. PATENT DOCUMENTS

| | | |
|---|---|---|
| 6,093,156 A | 7/2000 | Cunningham et al. |
| 2007/0293790 A1 | 12/2007 | Bainczyk et al. |

FOREIGN PATENT DOCUMENTS

| | | |
|---|---|---|
| EP | 1 118 856 A1 | 7/2001 |
| EP | 1 488 736 A1 | 12/2004 |
| EP | 1 507 143 A1 | 2/2005 |
| EP | 1 980 206 A1 | 10/2008 |
| WO | WO 96/30752 A1 | 10/1996 |
| WO | WO 00/19189 A1 | 6/2000 |
| WO | WO 01/23885 A1 | 4/2001 |
| WO | WO 03/082091 * | 10/2003 |
| WO | WO 03/083469 A2 | 10/2003 |
| WO | WO 03/100408 A1 | 12/2003 |

OTHER PUBLICATIONS

Copending Application JP 2008-517469 Office Action mailed Sep. 7, 2010.

* cited by examiner

*Primary Examiner* — Lyle Alexander
(74) *Attorney, Agent, or Firm* — Woodard, Emhardt, Moriarty, McNett & Henry LLP

(57) ABSTRACT

A test device for determining the concentration of at least one analyte in a sample using a element is proposed. The test device can be used particularly for glucose measurement, in particular blood glucose measurement, cholesterol measurement and/or coagulation measurement. The test device according to the invention comprises a housing with a closed state and an opened state, and a storage device for receiving at least one test element. The at least one test element is typically designed as a strip-shaped test element, and the storage device typically comprises a magazine. The magazine comprises a plurality of cavities, and the test elements are received substantially parallel to one another in the cavities. A measuring device and a dispensing device are also provided. The dispensing device comprises means for conveying the at least one test element from at least one storage position of the storage device during opening of the housing.

15 Claims, 14 Drawing Sheets

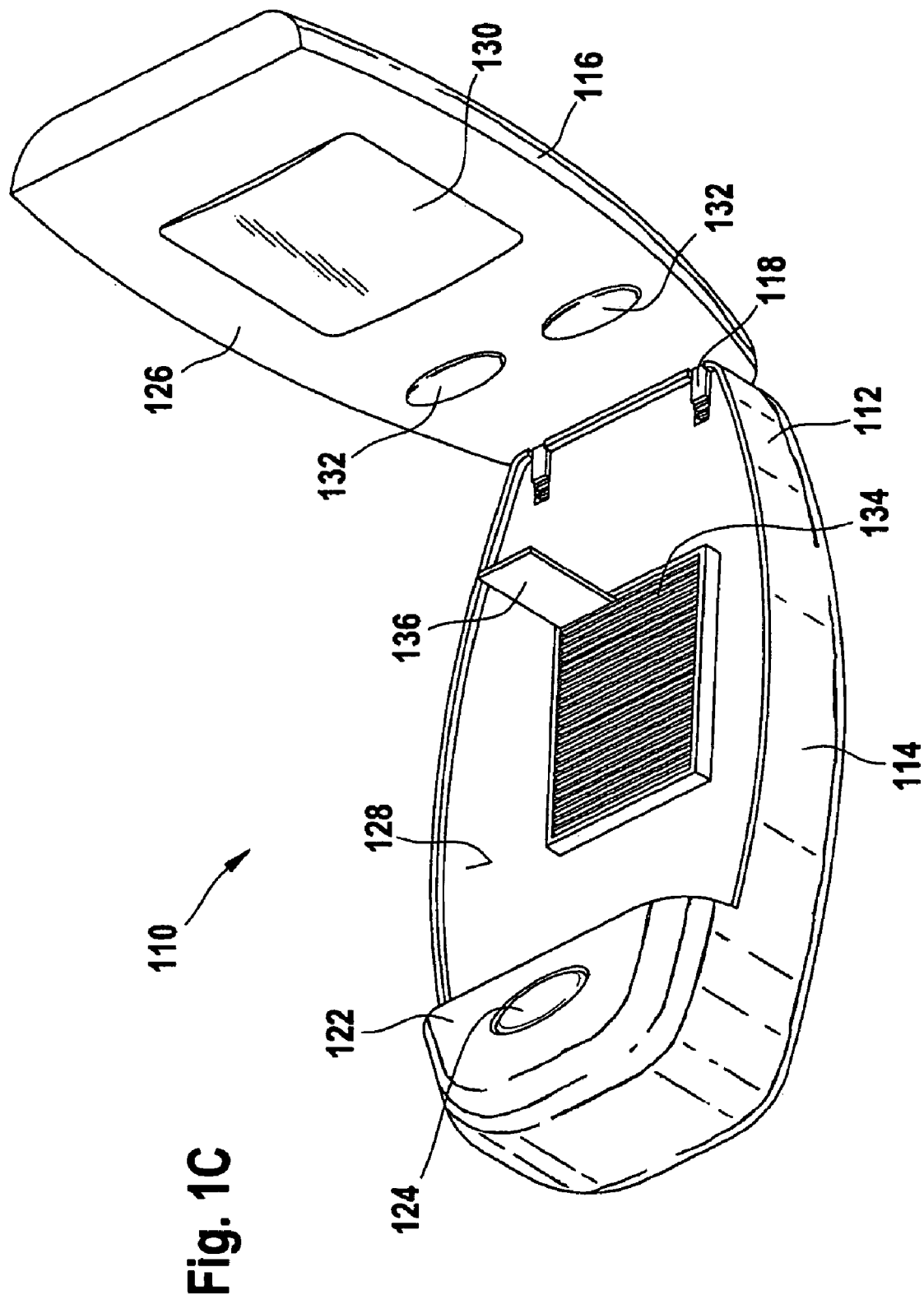

TEST DEVICE FOR DETERMINING AN ANALYTE CONCENTRATION

PRIORITY CLAIM

This application is a continuation of PCT Application No. PCT/EP2006/063208 filed Jun. 14, 2006, which claims the priority benefit of European Patent Application No. 05013396.6 filed Jun. 22, 2005.

FIELD OF THE INVENTION

The invention relates to a test device, in particular a portable test device, for determining at least one analyte concentration in a sample by means of a test element. The invention further relates to a test element for determining at least one analyte concentration in a sample using a test device according to the invention.

BACKGROUND

The monitoring of blood glucose concentration is an essential part of the daily routine of diabetics. The blood glucose concentration has to be determined quickly and reliably several times a day in order, if appropriate, to be able to take suitable medical measures. So as not to restrict the diabetic's daily routine any more than is necessary, suitable portable devices are often employed which are intended to be easy to carry around and to operate, such that the blood glucose concentration can be measured, for example at the workplace or even during leisure time.

Various portable devices are presently available on the market, some of them functioning according to different measurement methods, for example optical or even electrochemical measurement methods. An example of a frequently employed measurement method utilizes a special kind of electrochemical test strips. These test strips are, for example, configured such that a predetermined quantity of blood is conveyed to an electrode system via a capillary system on the test strip. For modern test strips, a quantity of blood of ca. 1.5 µl is sufficient, sometimes even quantities of blood of less than 1 µl. The electrode system may, for example, comprise metal electrodes that are provided with a reagent coating. The reagent coating in most cases contains different enzymes and so-called mediators and has the effect that charge carriers (for example in the form of redox molecules) form within the sample. The number of these charge carriers depends on the blood glucose concentration, and can be determined by means of the electrodes and a suitable measurement system, for example by means of a current-voltage measurement. From the amount of charge carriers, it is possible, finally, to calculate the blood glucose concentration. An example of electrochemical test strips of this kind is set out in U.S. Pat. No. 5,286,362, which is hereby incorporated by reference herein in its entirety.

As an alternative to the described electrochemical measurement method, other measurement principles can also be used. Thus, for example, WO 01/48461 describes a test strip with light guides for examining a sample, in particular of a body fluid, in which a reagent system, upon reaction with the sample, leads to a characteristic and optically measurable change in a detection zone. Light guides provided on the test strip allow the optical change to be remotely evaluated by an evaluation device.

The test strips thus form an important element of portable diagnostic systems. Typically, about 5 to 7 such test strips are needed each day by a diabetic. It is essential that the test strips are stored in a clean and dry condition, to ensure that the measurement of the blood glucose concentration is not rendered inaccurate by contamination or by the effect of moisture on the reagent coating or reagent system.

For this purpose, the test strips are usually stored in suitable containers in order then to be removed by the user from the test strip container for a measurement and fitted into a corresponding measuring device. Such measuring devices, for example measuring devices for electrochemical determination of the blood glucose concentration, are known to persons skilled in the art and are described, for example, in US 2002/0170823 A1 or in WO 96/30752, each of which is hereby incorporated by reference herein in their entireties.

However, the measuring systems known from the prior art, in which a blood glucose concentration is determined by means of a single test strip (single strip systems) and in which an individual test strip for a measurement has to be inserted into the device, have numerous disadvantages in practice. Such systems require numerous steps to be performed by the user or patient. A test strip has to be removed from a suitable storage device (e.g. a box of test strips) and then manually inserted into a measuring device. Thus, in order to permit secure handling by a patient, in particular by elderly patients or children, a corresponding test strip for single-strip systems of this kind can be made relatively large, in order to avoid the test strip slipping from the user's fingers and not being able to be used for a measurement. An increased size of the test strips, however, has the effect that the space taken up by the measuring systems increases and fewer test strips can be accommodated in a corresponding container. This increased space requirement also increases the material costs of the measuring systems.

The manual handling of the test strips is also associated with the disadvantage of increased risk of contamination of the test strips. Thus, manual removal of the test strips from a test strip container can expose the test strips to sweat on the fingers or to other forms of contamination that could impair a corresponding measurement. A further considerable disadvantage is that, each time the test strip container is opened, the test strips remaining in the test strip container are exposed to air moisture, with the result that test strips later removed from a test strip container will possibly have different properties than the test strips that were removed first.

In order to avoid the disadvantages of single-strip systems of this type, integrated systems have bean developed, in particular systems in which, in addition to a measuring device, a magazine for test strips is also incorporated. The systems can be designed in such a way that a test strip required for a measurement is in each case dispensed from the magazine to a measurement position. After application of the suitable sample thereto, for example a drop of blood, the measurement is then carried out directly.

Examples of integrated systems of this kind are described in WO 02/18940 A2, EP 1 488 736 A1, and EP 1 507 143 A1.

Compared to conventional single-strip systems, integrated systems have considerable advantages. For example, the number of steps needed to carry out a measurement is reduced, and it is also possible to use small, inexpensive test elements. The exposure of the test elements, in particular the test strips, to moisture and contaminants is also considerably reduced.

However, the integrated systems known from the prior art also have disadvantages, particularly disadvantages that detract from their use as portable devices and that reduce the level of acceptance by the patient. An important disadvantage is that the integration of the systems leads to comparatively large sizes of the devices. For example, for many integrated systems, bulky spring systems are needed to permit corresponding transport of test strips from a storage position to a measurement position. Other integrated systems may be driven by an electric motor, which requires even more space. By contrast, integrated systems not driven by electric motor require additional manual tensioning devices, which in many cases makes handling difficult, particularly for elderly patients or children. Moreover, the production costs of the systems are greatly increased when using electric motor drives or complex manual drives. Electrically driven systems additionally have the disadvantage that powerful batteries are needed for the electric motors, and these powerful batteries are expensive and have to be changed frequently. These batteries additionally lead to a further increase in the volume of the structure. A further disadvantage of the complex integrated systems known from the prior art is that these systems often have sensitive components on their surfaces, which components may easily be mechanically damaged, for example when the device is carried in a pocket, allow moisture to penetrate into the devices, and/or may be functionally impaired by contaminants.

While the foregoing describes systems designed for measuring blood glucose concentration, similar circumstances exist for other diagnostic and other analyte measuring devices and systems. It will be recognized that the shortcomings of the prior art and the objects of the present invention apply not just to blood glucose monitoring systems.

In view of the foregoing, it is an object of the present invention to provide a test device for determining at least one analyte concentration in a sample, in particular a liquid sample, by means of at least one test element, which test device avoids the disadvantages of the test devices known from the prior art. Moreover, another object is to provide corresponding test elements that can be used with the test device according to the invention.

SUMMARY OF THE INVENTION

These objects and others that may be apparent to those of ordinary skill in the art may be achieved by the embodiments of the present invention as described and claimed herein.

In one embodiment, a test device is provided for determining at least one analyte concentration in a sample by means of a test element. In exemplary embodiments, the device is configured to provide a glucose measurement, in particular a blood glucose measurement, and/or a cholesterol measurement and/or a coagulation measurement. Alternatively, or in addition, other analyte concentrations can also be determined or corresponding other analyses can be performed, for example pH measurements or similar chemical analyses or measurements. It is also possible, for example, to perform immunology measurements or similar measurements using the test device. The sample will in particular be a liquid sample, for example blood, urine, saliva or stools. However, other kinds of samples are also conceivable, for example gaseous samples. Moreover, instead of an analyte concentration, it is also possible to check simply for the presence or absence of an analyte, and this too may comprise an embodiment according to the present invention.

The test device generally comprises a housing, which has a closed state and an opened state. In one embodiment, the housing is configured to be opened manually by a user. In other embodiments, the housing can be designed such that it can be pushed open or folded open. For example, the housing can have a substantially cuboid shape with a fold axis, the housing being able to be folded open along the fold axis such that a bottom part of the housing and an upper part of the housing are at an angle to each other in the opened state, for example at a right angle. In the closed state, the bottom part of the housing and the upper part lie one on the other, such that the surfaces of the bottom part of the housing and the upper part that bear on each other are no longer accessible from the outside. In one embodiment, the surfaces of the bottom part of the housing and the upper part that bear on each other are sealed off by the housing in the closed state of the housing, for example in order to protect these surfaces and elements arranged on and/or in these surfaces (e.g. displays, operating elements, test strips, etc.) from environmental influences, e.g. air moisture, dirt or mechanical effects. Systems of this kind are known from the prior art, for example for cell phones. However, other configurations for opening and closing test devices according to the invention are also conceivable, for example slide devices.

By providing a housing that can be opened and closed by folding, sensitive components that are to be accessible to the user can be accommodated in an area of the housing that is accessible only in the folded-open or opened state of the housing.

Other embodiments of the test device further comprise a storage device for receiving at least one test element, said storage device providing a storage position for each such test element. In typical embodiments, the at least one test element is generally designed as a substantially flat test strip. The storage device comprises a magazine, such as an exchangeable magazine, which comprises a large number of cavities configured to receive a test strip. The test strips can be received substantially parallel to one another in the cavities, each mounted individually in a respective cavity of the storage device. In contrast to many devices known from the prior art, for example the device known from WO 02/18940 A2, this design of the storage device ensures that, when a test element is removed, the other test elements left in the storage device remain unaffected. In yet other embodiments, the storage device can comprise a desiccant in order to ensure dry and clean storage of the test elements. Thus, for example, a desiccant can be introduced into one or more cavities of the storage device. Alternatively, or in addition, a desiccant can also be introduced into another hollow space or a wall of the storage device. Alternatively, or in addition, the test elements can also comprise desiccants, for example sections that can absorb moisture.

In yet other embodiments, the test device according to the present invention comprises a measuring device. The measuring device is designed for using the at least one test element in order to determine the at least one analyte concentration. Measuring devices of this kind are known to persons skilled in the art and will therefore not be described in detail at this point. Typically, the type of measuring device depends on the type of test element used, the possible design of which will be described in more detail below. For example, the at least one measurement position can have electrical contacts for contacting the at least one test element for an electrochemical measurement.

In yet other embodiments, the test device further comprises a dispensing device. The dispensing device comprises means for conveying the at least one test element from a storage position to a measurement position. The dispensing device may be configured to cause this conveyance during opening of the housing. "Opening" of the housing can be understood as meaning the act of obtaining access to components that are concealed by the housing when in the closed state, for example surfaces of the bottom part and upper part of the housing that bear on each other, and operating elements (such as displays, operating buttons, test strip magazine) provided on these surfaces. For example, opening the test device can be understood as the housing being pushed open or folded open. Typically, a test strip dispenser is also made accessible, for example by means of a dispensing slot or the like being freed when the housing is opened.

In an exemplary embodiment, the conveying of a test element from a storage position to a measurement position can be triggered and/or effected by opening the housing. That is, the force needed for a user to open the housing can be utilized to convey the test element. For example, the force that is applied to the housing when opening the housing can be translated by means of a suitable mechanical device, for example a lever device, to a test element.

In other embodiments, the conveying of a test element by the dispensing device includes a rotational movement of the test element about a rotation axle. For a test element having a longitudinal aspect, for example a longitudinal axis of a test strip, the rotation of the test element during transport from the storage position to the measurement position takes place about a rotation axle perpendicular to the longitudinal axis of the test element. The dispensing device can thus comprise such a rotation axle. In one embodiment, the rotation axle extends through the at least one test element.

Alternatively, or in addition, the conveying of the test element from the storage position to the measurement position can also be effected by another form of movement, for example a translational movement. Thus, for example, a test strip can be pushed into a measurement position during opening of the housing. A combination of movements, for example a translational/rotational movement, is also possible.

The housing can be designed in such a way that, in the closed state of the housing, only non-sensitive components of the test device are accessible from the outside. For example, the housing can be provided on its outside with a smooth, dirt-repelling surface that prevents penetration of dirt and moisture into the test device. Alternatively, however, individual operating elements can also be arranged on the outer surface of the housing, for example individual operating buttons or indicator elements.

In yet other embodiments, the test device can be made shallow and can thus be carried inconspicuously. Furthermore, a disruptive motor noise or gear noise can be avoided, since it is possible to provided the test device without an electric motor. The system costs of the test device can be comparatively low, since costly component parts, e.g. motors, large batteries, etc., can be dispensed with. The material costs too, in particular for disposable material, can be comparatively low, since smaller test elements can be used.

To prepare for determination of an analyte concentration, for example a blood glucose concentration measurement, certain embodiments of the test device are simply opened, for example folded open. Tensioning of a transport device or actuation of an electric motor via a corresponding button is thus not necessary. This also ensures that patients with a limited range of movement, in particular elderly patients or children, can also safely handle the test device.

Embodiments of the test device according to the present invention can be additionally improved by various further features. For example, the storage device can comprise one or more magazines, such as exchangeable magazines. Such magazines can be obtained for example by the patient from a drugstore or by mail-order and inserted into the test device. These can be disposable magazines or reusable magazines. An electronic memory or similar type of data carrier can also be integrated, for example, into an exchangeable magazine, such that, when a new magazine is inserted into the test device, batch-specific data can be transmitted into the test device regarding the test elements contained in the magazine. These "non-evident coding systems" are known from the prior art.

In yet other embodiments, the storage device, for example the magazine, has a perforatable membrane, for example a film, for protecting (sealing) the at least one test element from air moisture and dirt. Thus, each cavity can be sealed off by a perforatable membrane of this kind. For example, the dispensing device and/or the at least one test element can be designed in such a way that, when the at least one test element is conveyed from the storage position to the measurement position during opening of the housing, the membrane is perforated. For this purpose, for example, the at least one test element can have a sharp edge or corner. In particular, the perforation can be effected by a rotational movement of the at least one test element in which, for example, a sharp edge of the at least one test element is pressed against the membrane until the latter is perforated, and the test element can be conveyed through the membrane into the measurement position.

According to the embodiments of the present invention, the test device can also be configured in such a way that, when the housing is closed, the at least one test element is conveyed from the measurement position back into the storage position. Typically, this conveying can also be effected by the dispensing device, which can have suitable means to permit this conveying. For example, this conveying can again involve a rotational movement of the at least one lest element. This aspect of the invention ensures that used test elements do not have to be removed, but instead are transferred back into the storage device, where they can be stored hygienically. Thus, separate disposal of each individual test element is not required. This also increases the discreetness with which the device can be used.

In yet other embodiments, the present invention further comprises a decoupling mechanism which, when so desired by the user, prevents the dispensing device from opening the test device. This can be achieved, for example, by simple decoupling of gears (e.g. decoupling of a toothed wheel connected to the housing from a toothed wheel connected to the dispensing device), in a way that is known to a person skilled in the art. Thus, for example, the housing can be opened without a test element being dispensed, if the user wishes this to be so and acts accordingly (for example by pressing a decoupling button). In this way, for example, a user can open the housing in order, for example, to read off electronic measurement results from a memory of the test device, without a test element being used. Alternatively, the housing can also be designed such that it can be opened only with a test element being dispensed.

Typically, the test device is designed in such a way that, during opening of the test device, an individual test element is conveyed into a measurement position. Alternatively, however, it is also possible for several test elements to be conveyed simultaneously into such measurement positions.

To ensure that a fresh test element, i.e. an unused test element, is used each time the housing is opened, the test device can additionally comprise a selector device. This selector device can be designed in such a way that a hitherto unused test element is selected each time the housing is opened. For example, test elements can be arranged parallel to one another in a row, for example in individual cavities, in which case the selector device travels one step in the direction of the next hitherto unused test element each time the housing is opened. For example, the selector device can in each case be moved on by one position of one cavity.

Generally, the test device according to the embodiments of the present invention can be used with a large number of types of test elements and test principles. Such test principles are known to the skilled person from the prior art. Thus, for example, optical measuring methods can be used, for example for optical determination of a cholesterol content in blood or urine, which is known for example from DE 698 15 207 T2, which is hereby incorporated herein by reference in its entirety. Alternatively, or in addition, electrochemical test strips can be used, as has already been described above in connection with blood glucose concentration measurements and is known for example from U.S. Pat. No. 5,286,362, which is hereby incorporated herein by reference in its entirety.

In connection with the test device according to the invention, embodiments of a test element are proposed according to the invention which can cooperate with the dispensing device of the test device. In one such embodiment, the test element has at least one connecting device for connecting the test element to the dispensing device. For example, this connecting device can be a hook that engages in a corresponding cutout in the dispensing device. In another example, the test element has an opening for the passage of an axle of the dispensing device. This opening can, for example, be a round or polygonal opening in the inner area of the test element, or said opening can also be an opening arranged at the edge of the test element, for example a cutout on the edge of the test element. In this way, the test element can be rotated by means of the axle, in order to transfer it from the storage position to the measurement position.

In other embodiments of the test element according to the present invention, the test element comprises a capillary system for conveying a liquid sample from an application site to a measurement site. For example, the test element can be designed in such a way that it has an opening for passage of an axle which, for example is arranged in the center of the test element or at the edge of the test element. The test element can also have an application site and electrode contacts at opposite ends. The test device can be designed in such a way that the test element is rotated from the storage position to the measurement position by the dispensing device during opening of the housing, as a result of which the application site becomes accessible to the user and, at the same time, the measurement electrodes of the test element engage the contacts of the test device. Thus, when the test element is conveyed into the measurement position, the test element is electrically contacted automatically.

Embodiments of the test device and the test element according to the present invention can be used by a patient according to the following exemplary sequence of steps: The patient carries the test device, in the closed state, in a corresponding transport container or in a pocket. To carry out a measurement, for example a blood glucose concentration measurement, the patient removes the test device from the pocket and opens the housing of the test device. Opening it can involve the device simply being folded open, for example, or additional actuation of an operating element may be necessary to open it. For example, the test device can have an opening button, which has to be actuated in order to open the test device. Inadvertent opening of the test device can be avoided in this way.

By opening the test device, a test element, for example a test strip, is conveyed automatically to a measurement position. In particular, the test element can be electrically contacted, for example. Moreover, the test device can also be designed in such a way that, during opening of the housing, the measuring device is automatically started. This starting of the measuring device can, for example, involve switching on a computer, for example a microcomputer integrated in the measuring device. Moreover, a suitable menu can automatically be presented to the user on an indicator element, for example a display. The housing can be designed in such a way that the computer is automatically switched off again when the test device is closed.

In the interim, the patient has provided a suitable sample. This provision of a sample can, for example, involve producing a drop of blood, for example by means of a lancet system known to a person skilled in the art. The patient applies the sample to the test element. The analyte concentration in the sample is then determined by a suitable measurement method, said determination being initiated automatically or initiated by the patient (e.g. by pressing a corresponding measurement button). The analyte concentration can be presented on an indicator element (e.g. a display) and/or stored in a data memory of a microcomputer. Alternatively, or in addition, the analyte concentration can be entered into a database, for example, and accordingly subjected to further data processing.

The patient then closes the housing of the test device again, with the used test element being conveyed back into the storage device, for example. The test device can then be stowed away again in a suitable transport device, for example in a pocket. Alternatively, or in addition, the data acquired, for example data including the analyte concentration, can be transferred to other evaluation devices, for example to other computer systems, or can be made available to a physician for further evaluation.

BRIEF DESCRIPTION OF THE DRAWINGS

The invention is described in more detail below on the basis of illustrative embodiments. However, the invention is not limited to the illustrative embodiments given here. The illustrative embodiments are shown schematically in the figures. Identical reference numbers in the individual figures designate elements which are identical or whose functions are identical, or which correspond to one another in terms of their function.

FIG. 1C illustrates the test device from FIG. 1A in the opened state;

DETAILED DESCRIPTION OF EMBODIMENTS OF THE PRESENT INVENTION

The following description of embodiments of the present invention is merely exemplary in nature and is in no way intended to limit the present invention or its application or uses.

Figure 1A:
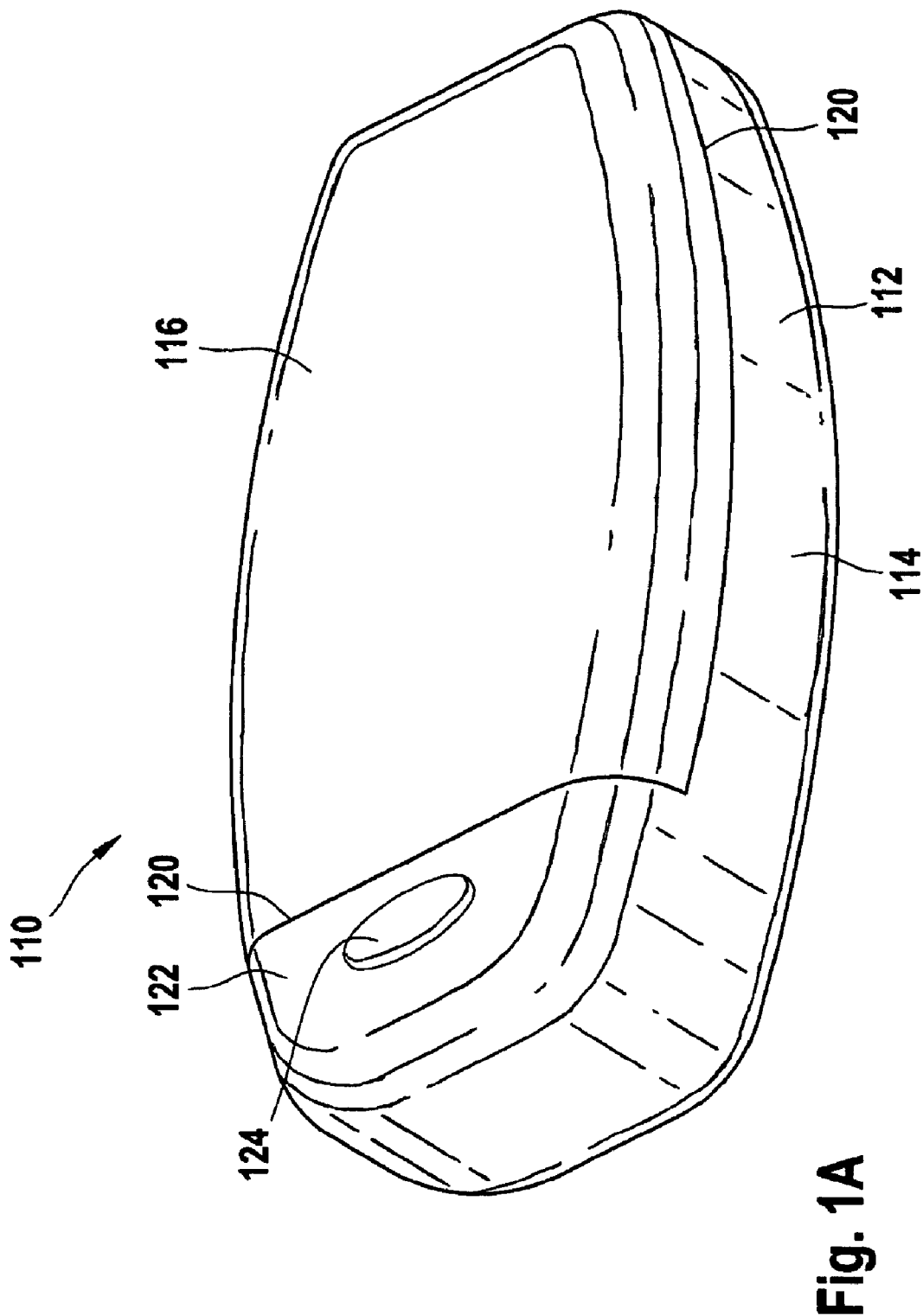
FIG. 1A illustrates a perspective view of one embodiment of a test device according to the present invention, in the closed state.
Figure 1B:
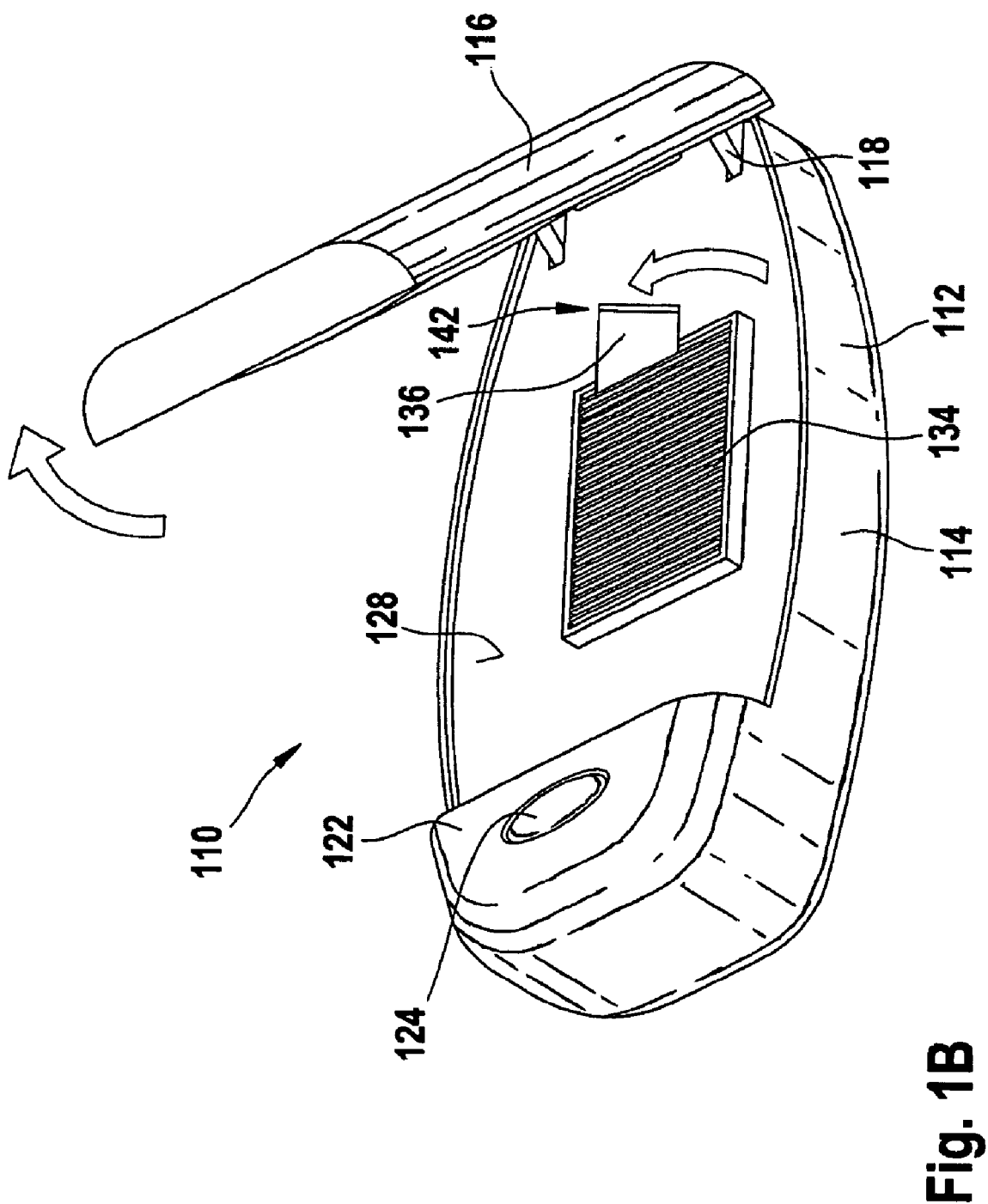
FIG. 1B illustrates the test device from FIG. 1A in the process of being opened.

A first illustrative embodiment of a test device 110 according to the invention for determining a blood glucose concentration is shown in FIGS. 1A to 1C. FIG. 1A shows the test device 110 in the closed state, FIG. 1B shows the test device 110 during opening, and FIG. 1C shows the test device 110 in the opened state.

In one embodiment, the test device 110 comprises a housing 112 with a bottom part 114 and a lid 116 (upper part of housing). The bottom part 114 and the lid 116 are connected to each other along a hinge 118, said hinge 118 at the same time being configured, in other embodiments, to translate force. This translation of force allows the force applied for opening the lid 116 to be used in means provided in the bottom part 114 of the housing for rotating a test strip (see below).

In the closed state shown in the embodiment of FIG. 1A, the housing 112 has a closed, smooth surface. The lid 116 and the bottom part 114 of the housing are adapted in shape to each other such that only a narrow separating line 120 is present through which generally no contaminants in the form of dirt and water can penetrate into the inside of the test device 110. The bottom part 114 or the housing has an upwardly pointing operating stage 122 which, during opening of the housing 112, can be gripped with the thumb of one hand. In this embodiment, a release button 124 is arranged on the operating stage 122. This release button 124 can have a purely mechanical function, such as the housing 112 being folded open when the release button 124 is pressed. Alternatively, or in addition, the release button 124 can also have an electrical function, e.g. causing measurement electronics and/or a microcomputer, in the test device 110 to be started or initialized.

In the interior of the housing 112 as shown, an operating surface 126 is located on the lid 116, and a measuring surface 128 is located on the bottom part 114 of the housing. The operating surface 126 comprises an indicator element in the form of a display 130 and one or more operating buttons 132. The operating buttons 132 can be used, for example, to start measurements and/or to call up menu functions of the test device 110. The display 130 can, for example, show analyte concentrations in digital form. Overall, the mode of operation of the test device 110 is comparable to known test devices that are available on the market.

Figure 3:
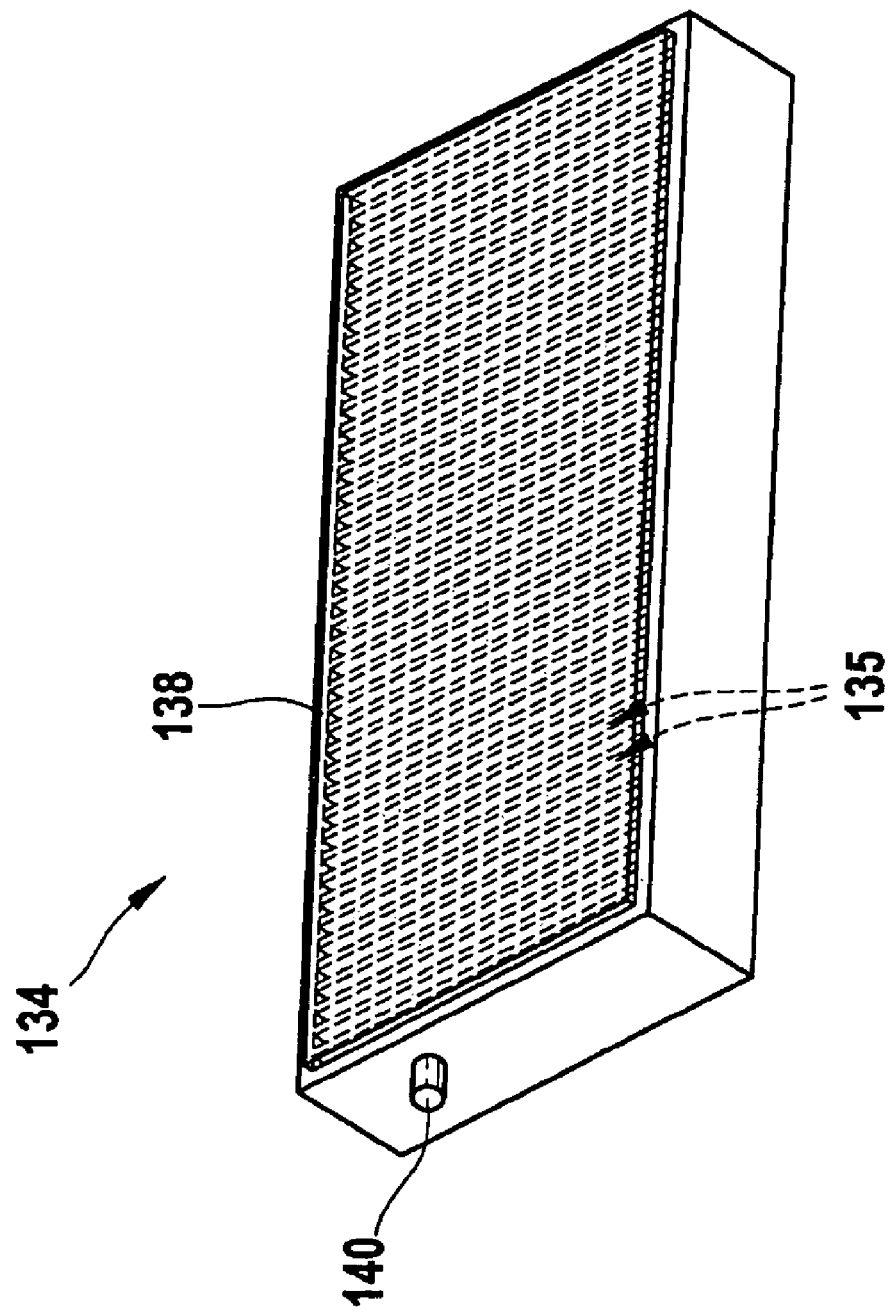
FIG. 3 illustrates a perspective view of an embodiment of a test strip magazine for use in a test device according to the present invention.

In one embodiment, a tray- or rack-shaped magazine 134 is received within the measuring surface 128 in the bottom part 114 of the housing. The magazine 134 can be designed to be exchangeable and has a plurality of cavities 135 in which test strips 136 are received parallel to one another. In other embodiments, the magazine 134, including the cavities 135, can contain a desiccant (not shown), by which the test strips 136 received in the cavities 135 are protected from the influence of air moisture. An example of such a magazine 134 is shown in FIG. 3. In the illustrated embodiment, a membrane in the form of a sealing film 138 is applied over each cavity 135. The magazine 134 also comprises a rotation axle 140 around which the individual test strips 136 are mounted so as to be able to rotate.

In an exemplary embodiment of the present invention, during opening of the housing 112 of the test device 110 (compare FIG. 1B), a test strip 136 is in each case rotated about the rotation axle 140 by means of a dispensing device 160. A sealing film 138 of the associated cavity 135 is broken open or pierced by an edge 142 of the test strip 136. When the housing 112 is folded completely open (compare FIG. 1C), the test strip 136 is located in a generally upright position for sample application and measurement. Alternatively, other orientations of the test strip 136 for sample application and/or measurement are possible, for example a separate application position and measurement position. It is also conceivable that, after the housing 112 is folded open, the test strip 136 is first conveyed to an application position and then, after the sample has been applied, to a measurement position, the latter action being triggered, for example, by re-closure of the housing 112. The only general requirement is that, in the application position, an application site 150 of the test strip (see below, FIGS. 4A and 4B) is accessible to the patient for applying, a sample. Once sample is applied, further conveyance, if needed (that is, if the sample application position is different than the measurement position), to a measurement position may be accomplished as desired.

In the application and measurement position shown in the embodiment of FIG. 1C, the upright test strip 136 is electrically contacted by contacts (see for example reference number 176 in FIG. 5A) of the test device 110, such that an electrochemical measurement can be performed.

The magazine 134 shown in FIG. 3 can be designed as a tray or rack for 10, 25, 50 or more test strips 136, for example. The limitation on the number of test strips 136 lies in the size of the test device 110. In one embodiment, a magazine length of around 40 mm is needed for 50 test strips 134. Test strips according to the invention, which can be fitted in a magazine 134 according to the embodiment in FIG. 3, are shown by way of example in FIGS. 4A and 4B. In the illustrative embodiment shown in FIG. 4A, the test strip 136 has at its center a hole 144 for receiving the rotation axle 140 (see FIG. 3). In the illustrative embodiment of the test strip 136 shown in FIG. 4B, a notch 146 is located on an edge of the test strip 136. Both the hole 144 and the notch 146 allow the test strip 136 to be rotated about the rotation axle 140 of the magazine 134 from a storage position to a measurement position.

Figure 4A:
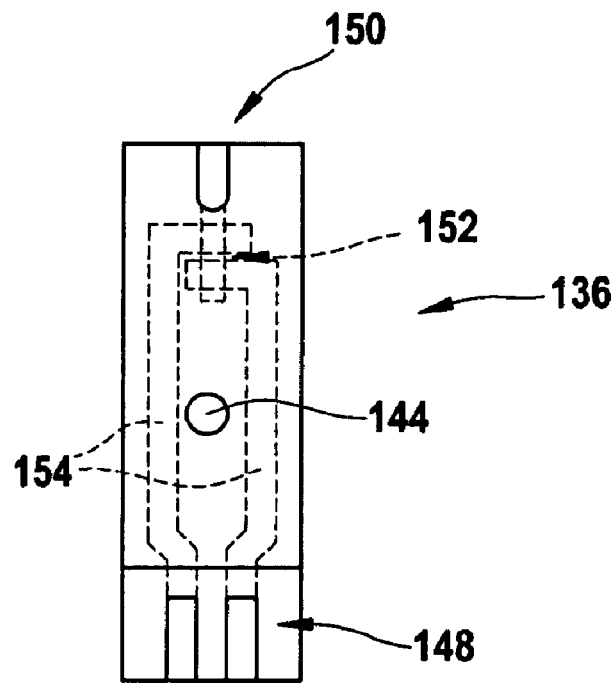
FIG. 4A illustrates a plan view of one embodiment of a test strip according to the present invention.
Figure 4B:
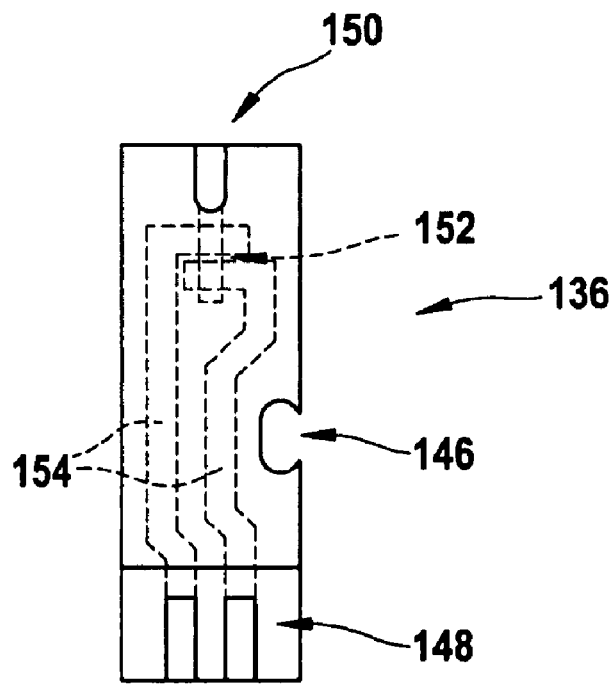
FIG. 4B illustrates a plan view of another embodiment of a test strip according to the present invention.

The test strips 136 in the illustrative embodiments according to FIG. 4A and FIG. 4B are electro-chemical measurement strips for measuring blood glucose concentration in accordance with the description above. The test strips 136 are designed as elongate rectangles and have electrode contacts 148 at one end and, at an opposite end, an application site 150 for application of a drop of blood. Blood is conveyed from the application site 150 to the interior of the test strip 136 via a capillary system 152. There, the blood comes into contact with measuring electrodes 154, which in turn are connected to the electrode contacts 148. In the measurement position (shown in FIG. 1C), the electrode contacts 148 are connected to corresponding contacts of the test device 110, such that an electro-chemical determination of the blood glucose concentration can be carried out.

Typically, in addition to the dispensing device 160 for conveying the test strip 136 to the measurement position (compare FIGS. 1B and 1C), the housing 112 of the test device 110 also contains an evaluation device. In the illustrated embodiments, this evaluation device serves to evaluate the test strips 136 by means of an electrochemical measurement. Such evaluation electronics are known to a person skilled in the art. Moreover, the evaluation electronics can also comprise a microcomputer, which can be operated via the operating buttons 132, for example. The microcomputer can control corresponding evaluation routines and can, for example, comprise a data memory. Other embodiments not shown for an evaluation device serve to evaluate by means of an optical measurement.

In the illustrative embodiment of the test device 110 shown in FIGS. 1A to 1C, the display 130 and the operating buttons 132 are integrated in the operating surface 126 of the lid 116. As has been described above, opening the housing 112 can, for example, automatically switch the test device 110 on. Alternatively, or in addition, this switching-on can also be effected via the release button 124 (which can also be designed as an "on/off button"). After the test device 110 has been used, e.g. after the blood glucose concentration has been measured, the patient closes the housing 112 again by folding the lid 116 shut. By doing so, the test strip 136 is automatically pivoted back into its cavity 135. Alternatively, the test strip 136 can also be removed manually and disposed of. During closure of the housing 112, the test device 110 can also be automatically switched off, thus ensuring that the test device 110 does not inadvertently remain switched on. This saves electrical energy.

Figure 2A:
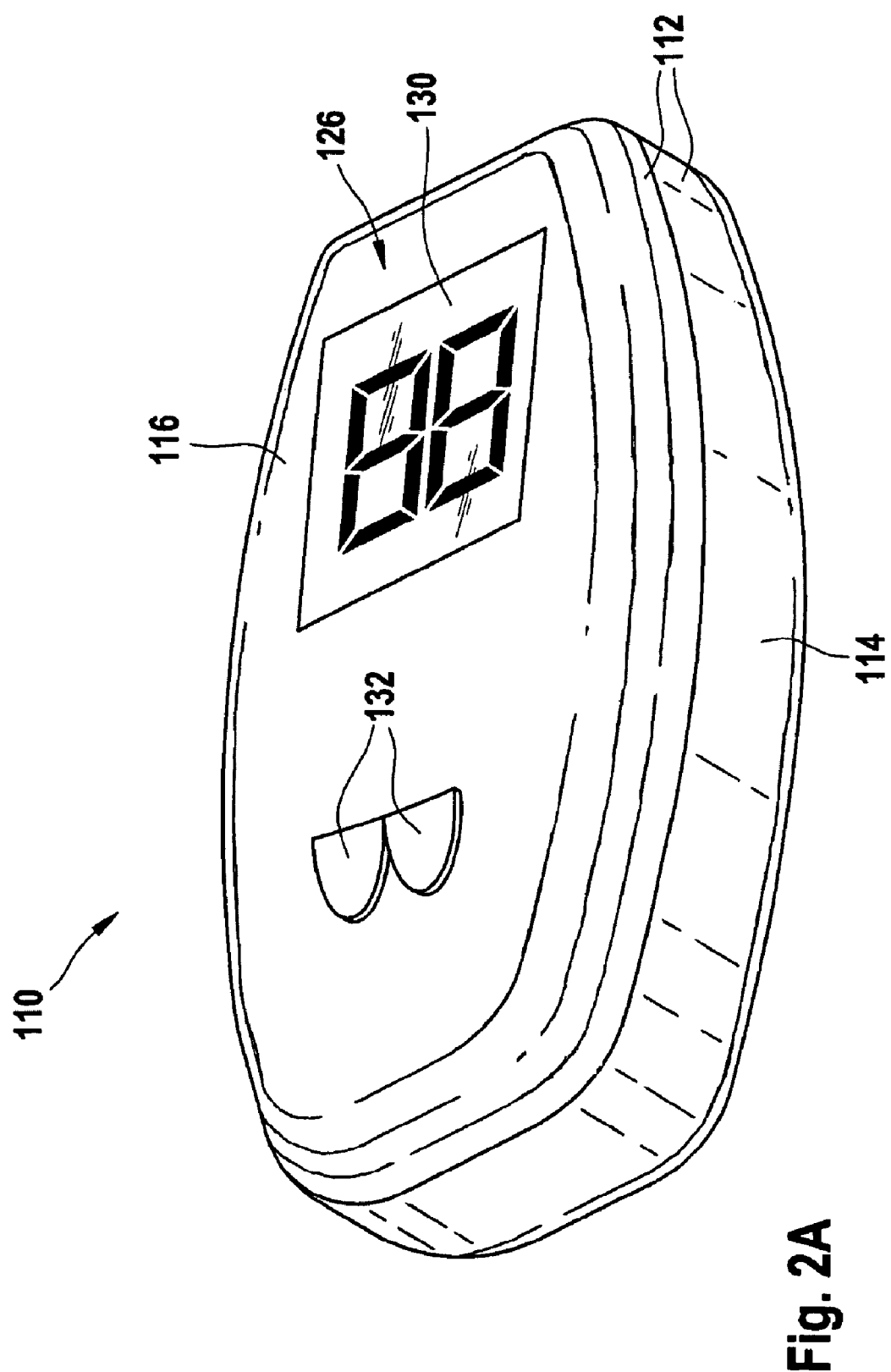
FIG. 2A illustrates a perspective view of another embodiment of a test device according to the present invention, in the closed state.
Figure 2B:
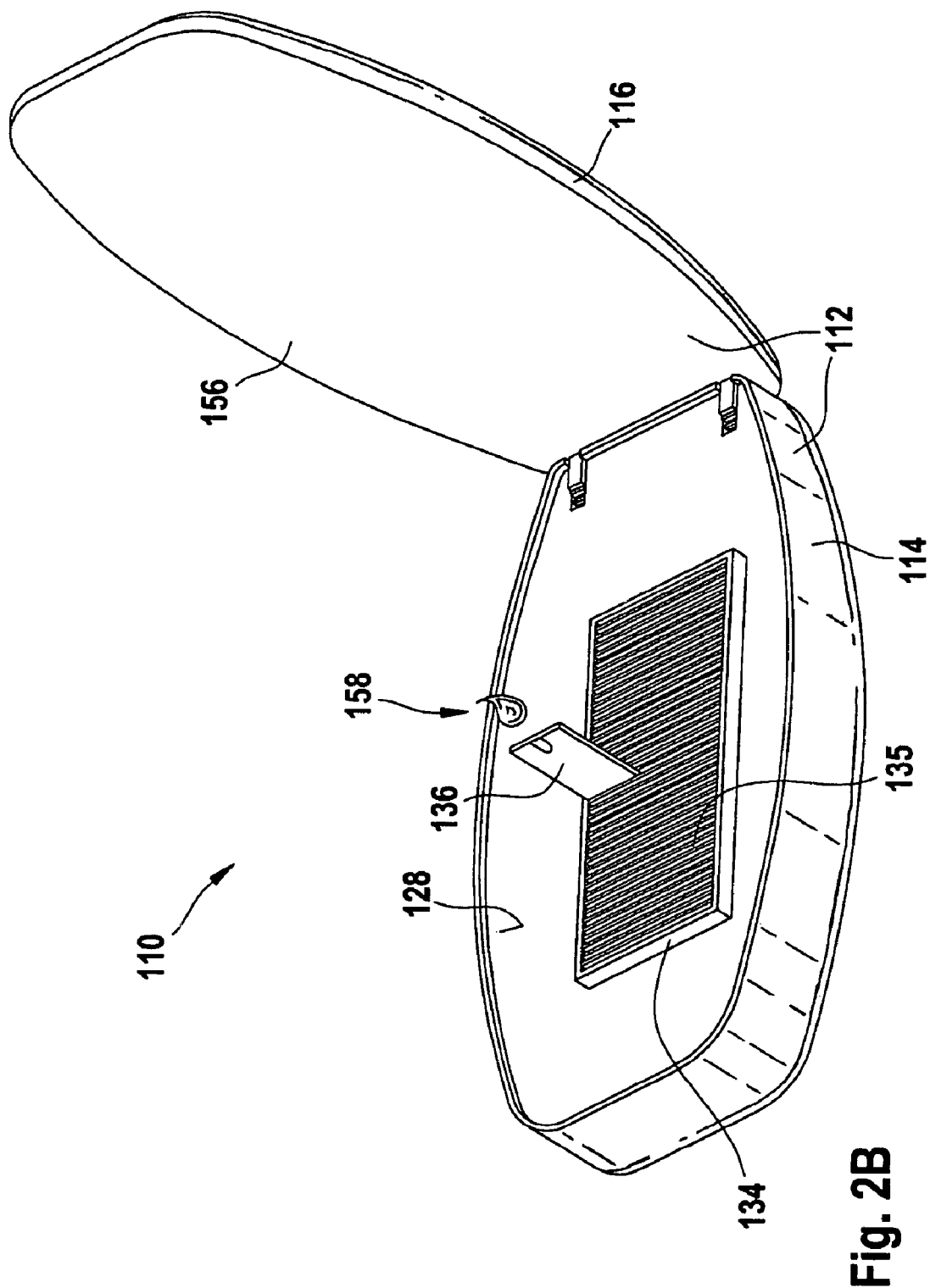
FIG. 2B illustrates the test device from FIG. 2A in the opened state.

FIGS. 2A and 2B show an alternative illustrative embodiment 110 to the one in FIGS. 1A to 1C, which alternative illustrative embodiment has a similar mode of operation. Once again, a magazine 134, for example a magazine according to the embodiment in FIG. 3, is received within a housing 112. The magazine 134 again has cavities 135 in which test strips 136 are fitted. The test strips 136 can again be designed analogously to the illustrative embodiments in FIG. 4A or 4B.

In contrast to the embodiment according to FIGS. 1A to 1C, the illustrative embodiment according to FIGS. 2A and 2B has a measuring surface 128 lying in the inside of the housing 112, but no internal operating surface 126. Instead, in this illustrative embodiment the operating surface 126 with a display 130 and operating buttons 132 is on the top face of the lid 116. Functions in the form of indicator elements and/or operating elements (not shown) can also be optionally accommodated on the inner side 156 of the lid.

The function of the test device 110 according to the illustrative embodiment in FIGS. 2A and 2B can, for example, be such that a patient opens the housing 112 and applies a drop of blood 158 to the test strip 136. The housing 112 is then closed again, as a result of which, for example, a measurement is started automatically or continued, or electronic measurement results are evaluated, the results again being able to be read from the display 130 when the housing 112 is closed.

FIGS. 5A to 5E are schematic representations showing embodiments of a test strip 136 being dispensed by a dispensing device 160 according to the invention during opening of the housing 112 of a test device 110 according to the depiction in FIGS. 1A to 1C, for example. The view in FIGS. 5A to 5E shows a cross section parallel to the hinge 118 (that is to say perpendicular to the longer axis of the housing 112) through the bottom part 114 of the housing of the test device 110. To simplify matters, the housing 112 is not shown in FIGS. 5A to 5E.

The dispensing device 160 interacts with a magazine 134, for example according to the view in FIG. 3. Several test strips 136, in this illustrative embodiment test strips 136 according to the illustrative embodiment in FIG. 4A, are received in the magazine 134. The test strips 136 have electrode contacts 148 at one end and, at the opposite end, an application site 150 for application of a drop of blood 158. Moreover, the test strips 136 each have a hole 144 through which a rotation axle 140 is guided. The bottom part 114 of the housing of the test device 110 is in this case designed in such a way that it has a seat for receiving the ends of the rotation axle 140. This receiving seat is not shown in FIGS. 5A to 5E. The rotation axle 140 thus represents a component part of a magazine 134, and, when a new magazine 134 is introduced into a housing 112 of a test device 110, the ends of the rotation axle 140 are each locked or engaged in corresponding receiving seats in the housing 112. Each test strip 136 is thus mounted so as to rotate about this rotation axle 140.

Figure 5A:
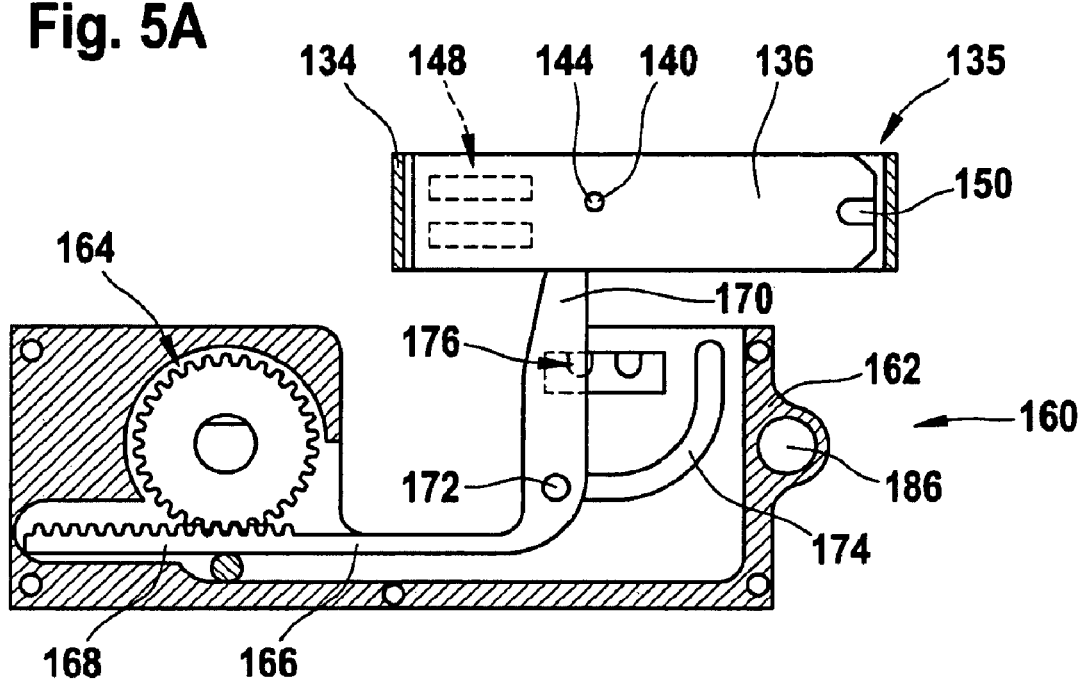
FIGS. 5A to 5E illustrate a front plan view of an embodiment of a dispensing device in a schematic sequence for conveying a test strip from a storage position to a measurement position during opening of a test device.
Figure 5B:
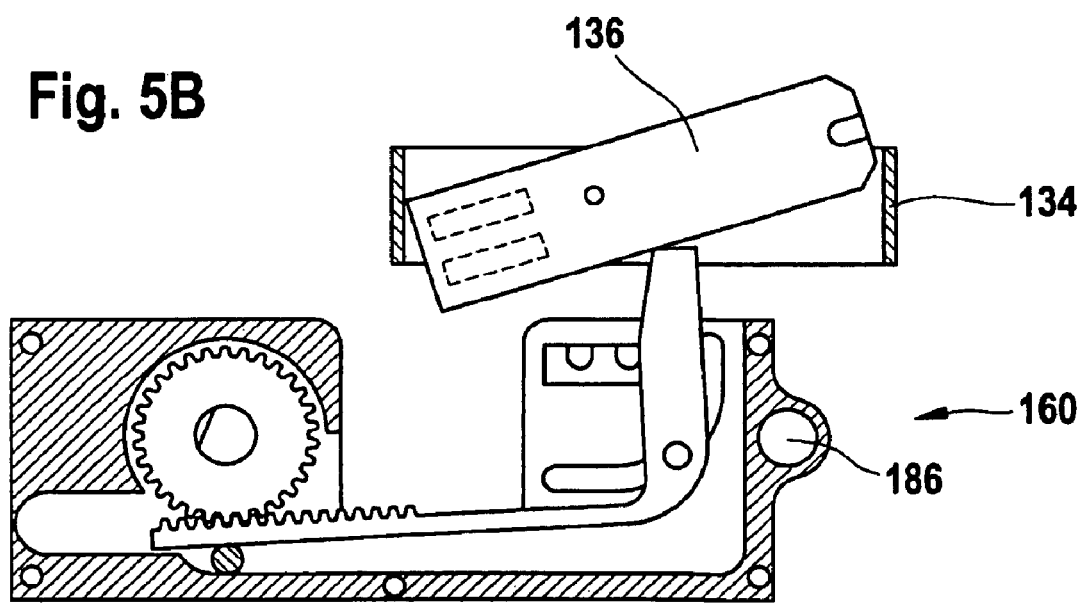
Figure 5C:
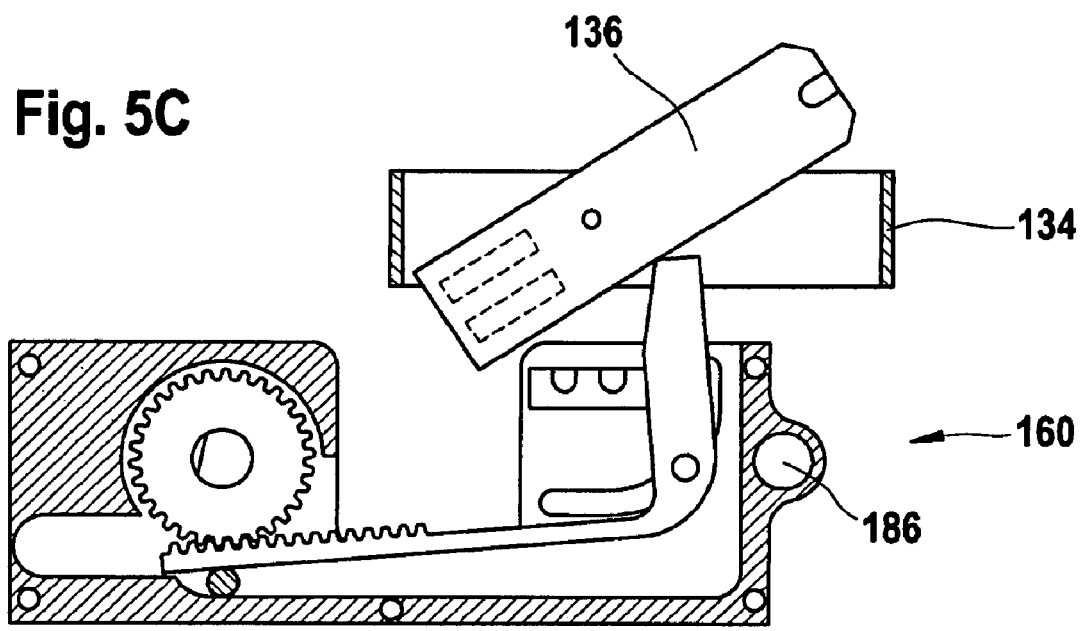
Figure 5D:
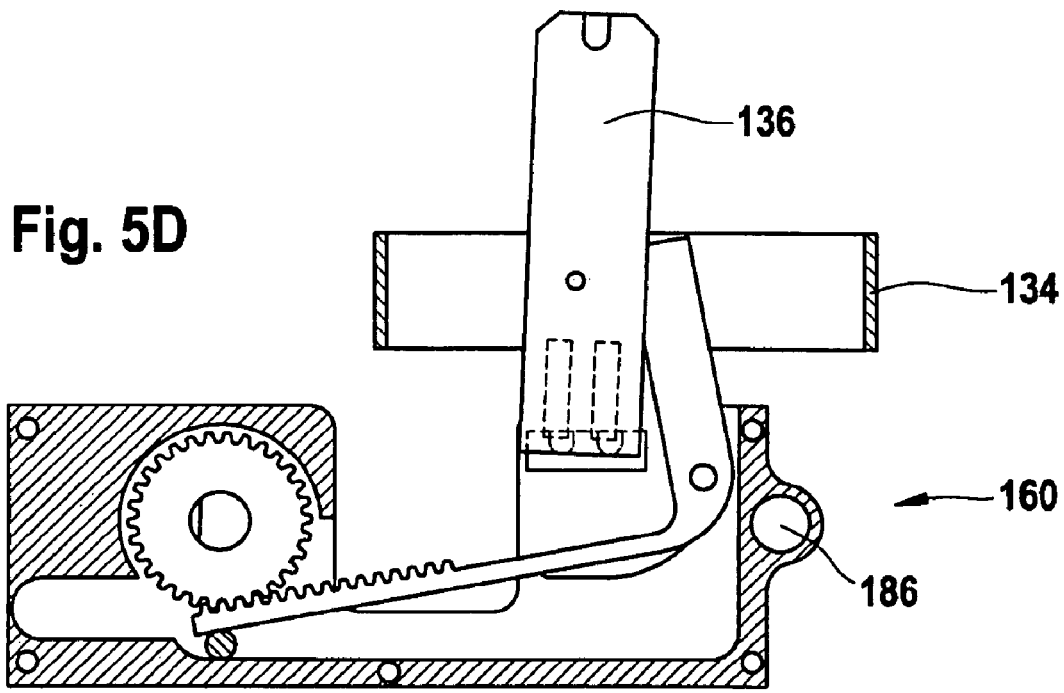
Figure 5E:
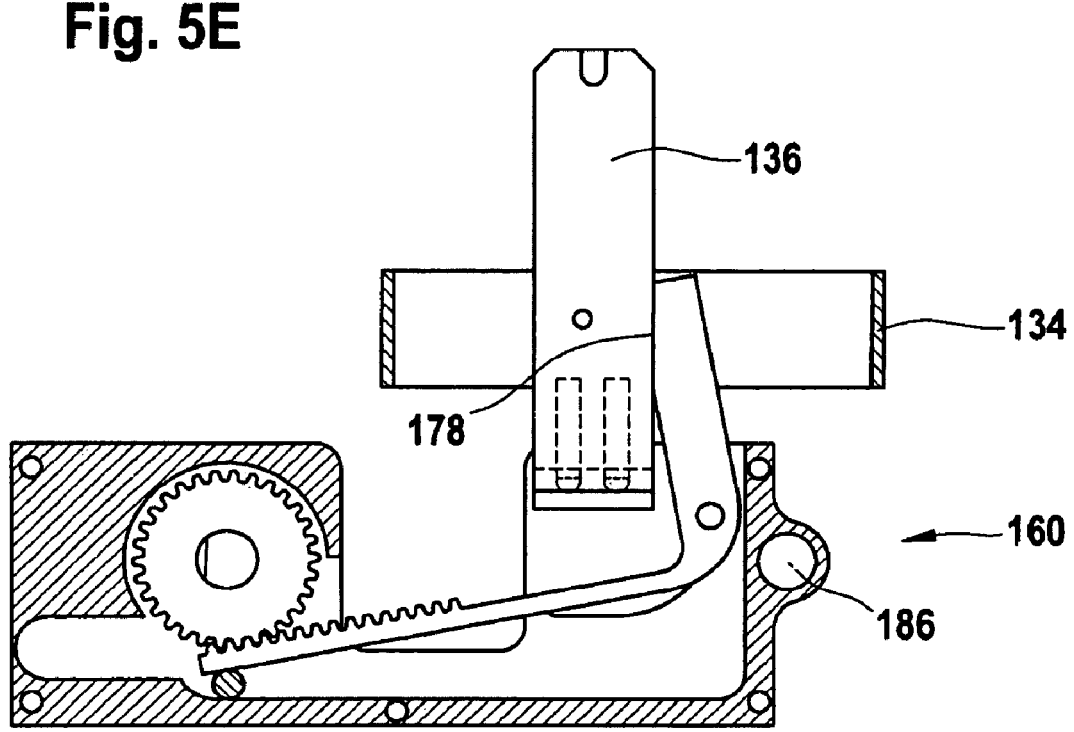

According to certain embodiments of the present invention, the dispensing device 160 is provided to convey a test strip 136 from a storage position (illustrated in FIG. 5A) to a measurement position (illustrated in FIG. 5E). When the housing 112 is closed (compare view in FIG. 1A), the test strip 136 is located in the storage position shown in FIG. 5A, whereas, when the housing 112 is opened, the test strip 136 is located in the measurement position shown in FIG. 5E. In the storage position shown in FIG. 5A, the test strip 136 is received in a cavity 135. In the measurement position shown in FIG. 5E, by contrast, the test strip 136 is rotated through 90° compared to the storage position according to FIG. 5A, and the electrode contacts 148 point downward, and the application site 150 points upward.

For this purpose, in certain embodiments the dispensing device 160 has a dispensing housing 162, which is arranged underneath the magazine 134. In the dispensing housing 162, a toothed wheel 164 with a rotation axle is mounted rotatably perpendicular to the plane of the drawing. This toothed wheel 164 is driven by means of a gear (not shown) translated through the hinge 118 of the test device 110 and rotates counterclockwise during opening of the housing 112.

The dispensing device 160 also comprises a transport arm 166, which is bent at a right angle. In a drive area 168, the transport arm 166 cooperates with the toothed wheel 164 in such a way that, during opening of the housing 112, the transport arm 166 is moved to the right in FIG. 5A by the toothed wheel 164.

In the storage position shown in FIG. 5A, which represents a closed housing 112 of the test device 110, an upwardly pointing press area 170 of the transport arm 166 lies at the base of the magazine 134. The transport arm 166 is guided within the dispensing housing 162 of the dispensing device 160 via a pin 172 and a curved oblong hole 174, such as a cam follower and a cam slot.

As soon as the housing 112 of the test device 110 is slightly opened, the press area 170 of the transport arm 166 begins to penetrate into the magazine 134 (see FIGS. 5B to 5E). In doing so, the press area 170 penetrates in each case into exactly one cavity 135 of the magazine 134, and exactly one test strip 136 is pressed out of the magazine 134. For this purpose, the magazine 134 can, for example, have a perforatable membrane 138 (see FIG. 3) above and underneath each cavity 135. This membrane can be pierced by the edges of the test strip 136 and/or by the press area 170 of the transport arm 166. When the housing 112 is opened, the toothed wheel 164 moves the transport arm 166 to the right in FIGS. 5A to 5E across the drive area 168, as a result of which the press area 170 moves upward into the magazine 134. The magazine 134 is mounted over the dispensing device 160 in such a way that the press area 170 acts on the test strip 136 to the right of the rotation axle 140. In this way, the test strip 136 in the views in FIGS. 5A to 5E is rotated counterclockwise.

In this illustrative embodiment according to FIGS. 5A to 5E, the dispensing device 160 also comprises contacts 176 for contacting the test strip 136. These contacts 176 are connected to measurement electronics of the test device 110. These measurement electronics, which are not shown, permit evaluation of a test strip 136 by electrochemical measurement methods that are known to a skilled person from the prior art. For example, these measurement electronics can include electronics for a current-voltage measurement or a capacitive measurement. The contacts 176 are fixed on the dispensing housing 162 of the dispensing device 160 in such a way that the contacts 176 in the measurement position shown in FIG. 5E make contact with the electrode contacts 148 of the test strip 136. For example, the contacts 176 can have a corresponding clamping device into which the test strip 136 is pressed by the dispensing device 160, in particular by the transport arm 166. In this way, a safe and reliable electrical contact can be established between electrode contacts 148 and contacts 176.

Because of the curved oblong hole 174, the press area 170 of the transport arm 166 describes a curved trajectory, for example an arc of a circle, during opening (sequence of FIGS. 5A to 5E). During closure of the housing 112, this arc of a circle is traveled by the press area 170 in the reverse direction (sequence of FIGS. 5E to 5A). The press area 170 thus lies with a flattened area 178 on the test strip 136, such that the test strip 136 is forced to rotate clockwise when the housing 112 is closed. In this way, after use of the test strip 136, the used test strip 136 is transferred back from the measurement position (FIG. 5E) to the storage position (FIG. 5A).

The dispensing device 160 shown in FIGS. 5A to 5E represents a mechanism for dispensing exactly one test strip 136 at a time from the magazine 134. Depending on the position of the dispensing device 160 underneath a specific cavity 135 of the magazine 134, it is precisely the test strip 136 situated in the corresponding cavity 135 that is transferred to the measurement position (see FIG. 5E).

Figure 6A:
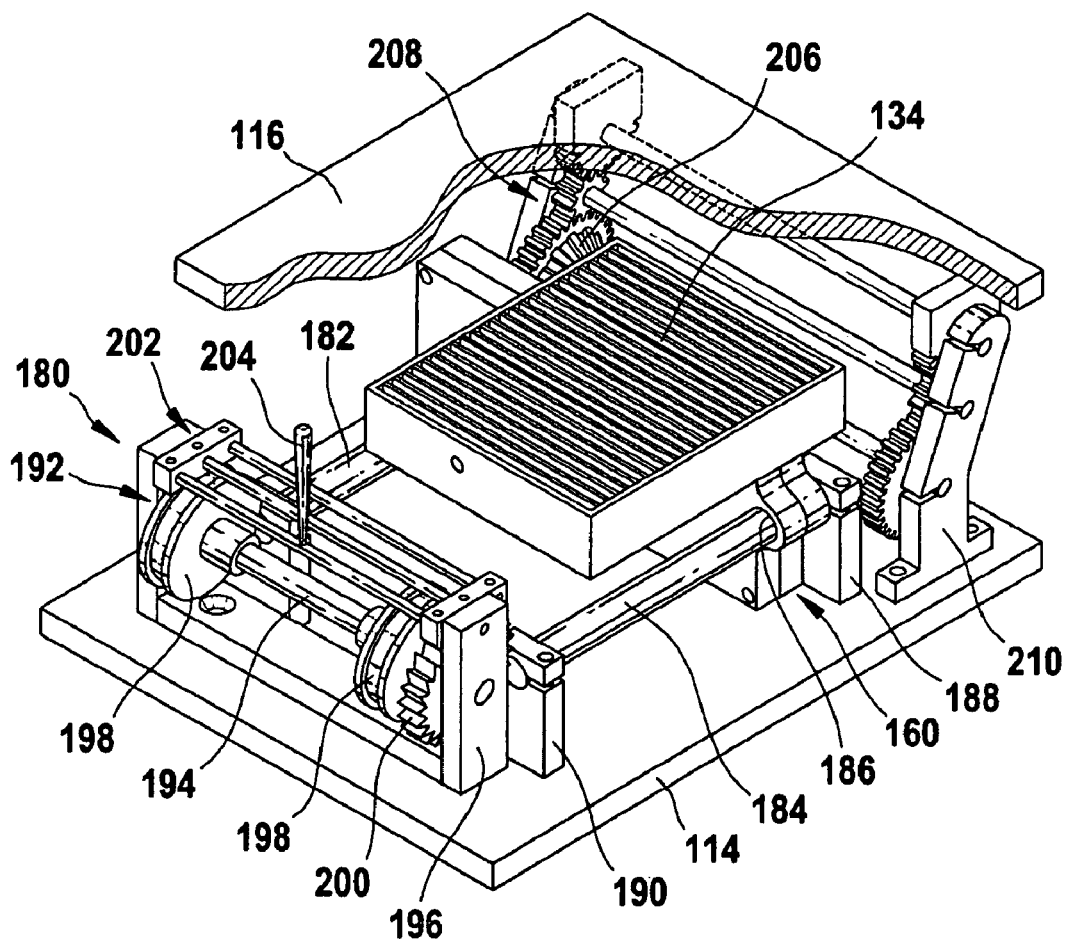
FIGS. 6A to 6D illustrate perspective and side plan views of an embodiment of a selector device for selecting a test strip from the magazine.
Figure 6B:
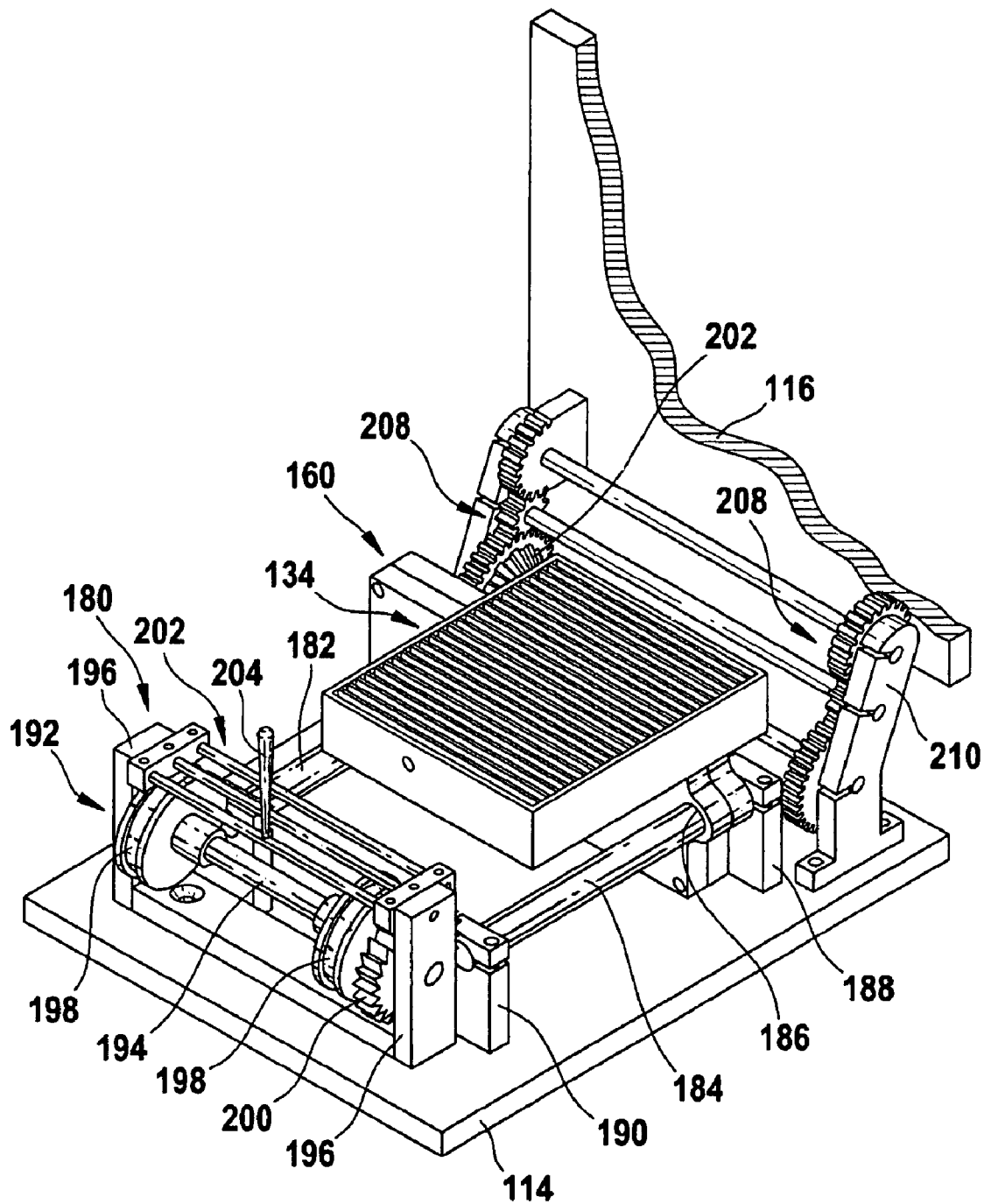
Figure 6C:
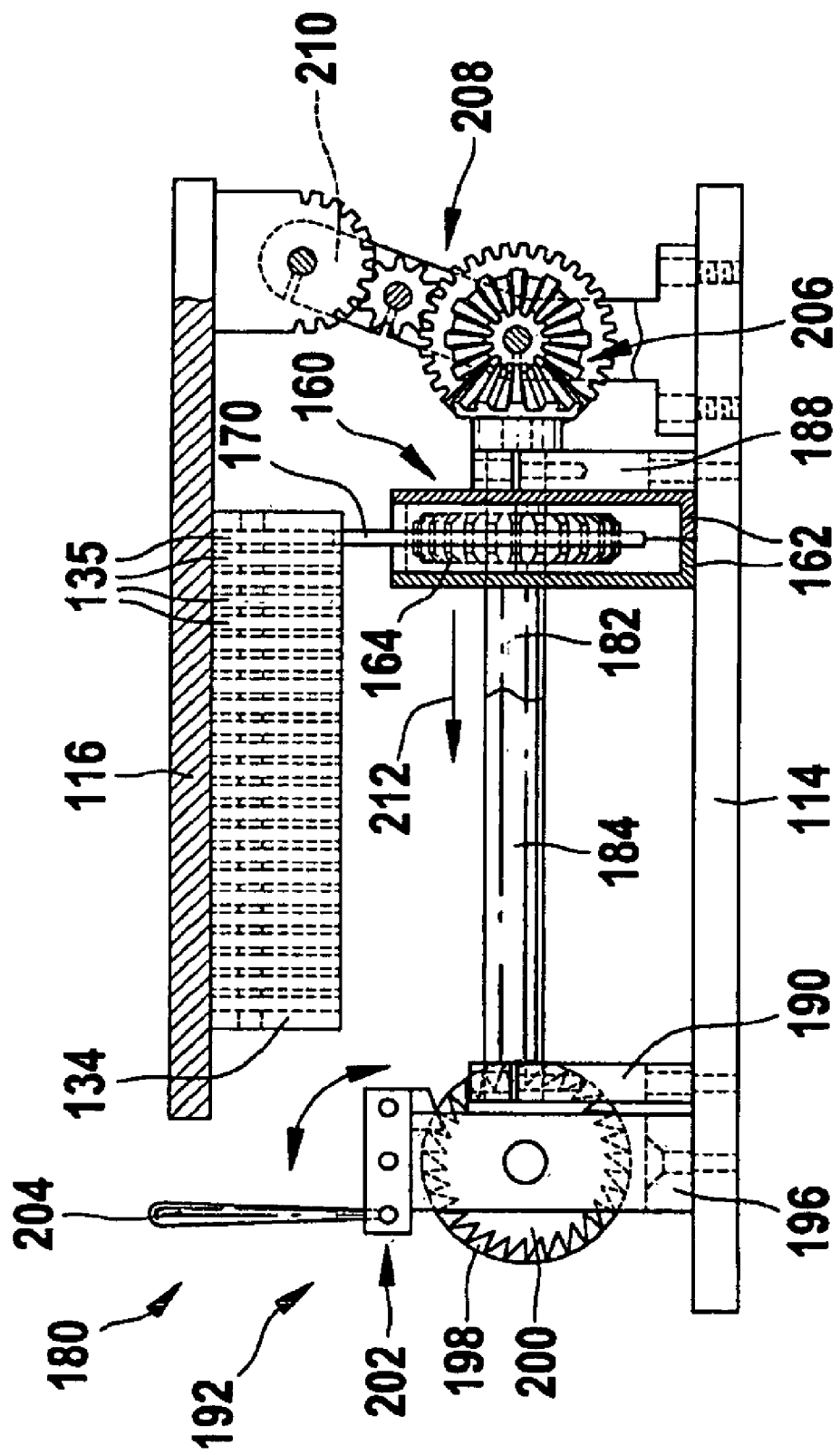

The test device 110 can comprise a mechanism which permits selection of a specific cavity 135 of the magazine 134. An example of an embodiment of such a selector device 180 is shown schematically in different views in FIGS. 6A to 6D. FIG. 6A shows a perspective partial view with the lid 116 closed, FIG. 6B shows a perspective partial view with the lid 116 opened. FIG. 6C shows a side view with the lid 116 closed, and FIG. 6C shows a side view with the lid opened. FIGS. 6A to 6C will be explained by comparing them.

The dispensing device 160 according to the above illustrative embodiment described in FIGS. 5A to 5E is mounted on two shafts 182, 184, namely a drive shaft 182 and a slide shaft 184, which are component parts of the selector device 180. The drive shaft 182 is connected to the toothed wheel 164 of the dispensing device 160 and drives it. The slide shaft 184 extends through a corresponding slide shaft bore 186 in the dispensing housing 162, such that the dispensing device 160 is able to slide on the slide shaft 184. A lid-side (that is to say on the right in FIGS. 6A to 6D) abutment position of the dispensing device 160 is defined by an abutment 188 which is connected fixedly to the bottom part 114 of the housing and which also at the same time supports the lid-side end of the slide shaft 184. The opposite end of the slide shaft 184 is held in a holder 190.

In one embodiment, the selector device 180 further comprises a drive unit 192. The drive unit 192 for its part comprises a transverse shaft 194, which is mounted on two side holders 196 and extends perpendicular to the shafts 182, 184. Two drums 198 and a balance wheel 200 are secured on the transverse shaft 194. The transverse shaft 194 is pretensioned by a spring (not shown). Moreover, the drive unit 192 has a rocker 202 with a trigger lever 204. This trigger lever 204 is connected to the release button 124 (compare FIG. 1A, for example). When the trigger lever 204 is actuated, the rocker 202 briefly frees the balance wheel 200, such that the latter, driven by the spring, can move forward by exactly one catch (corresponding to one tooth on the balance wheel 200).

A spring band (not shown in the figures) is wound onto the drums 198 and is in turn connected to the dispensing device 160. When the balance wheel 200 turns, the drums 198 thus also turn, as a result of which the spring band is wound onto the drums. In this way, the dispensing device 160 is moved in the direction of movement 212, that is to say to the left in FIGS. 6A to 6D.

For each catch of the balance wheel 200, that is to say for each actuation of the trigger lever 204, a defined movement of the dispensing device 160 takes place by one step. As has been described above, the magazine 134 is arranged over the dispensing device 160. The balance wheel 200 and the gearing provided by the drums 198 are such that one movement step signifies a forward positioning by exactly one cavity 135. Thus, for each catch, the dispensing device 160 is conveyed forward by one cavity 135.

Figure 6D:
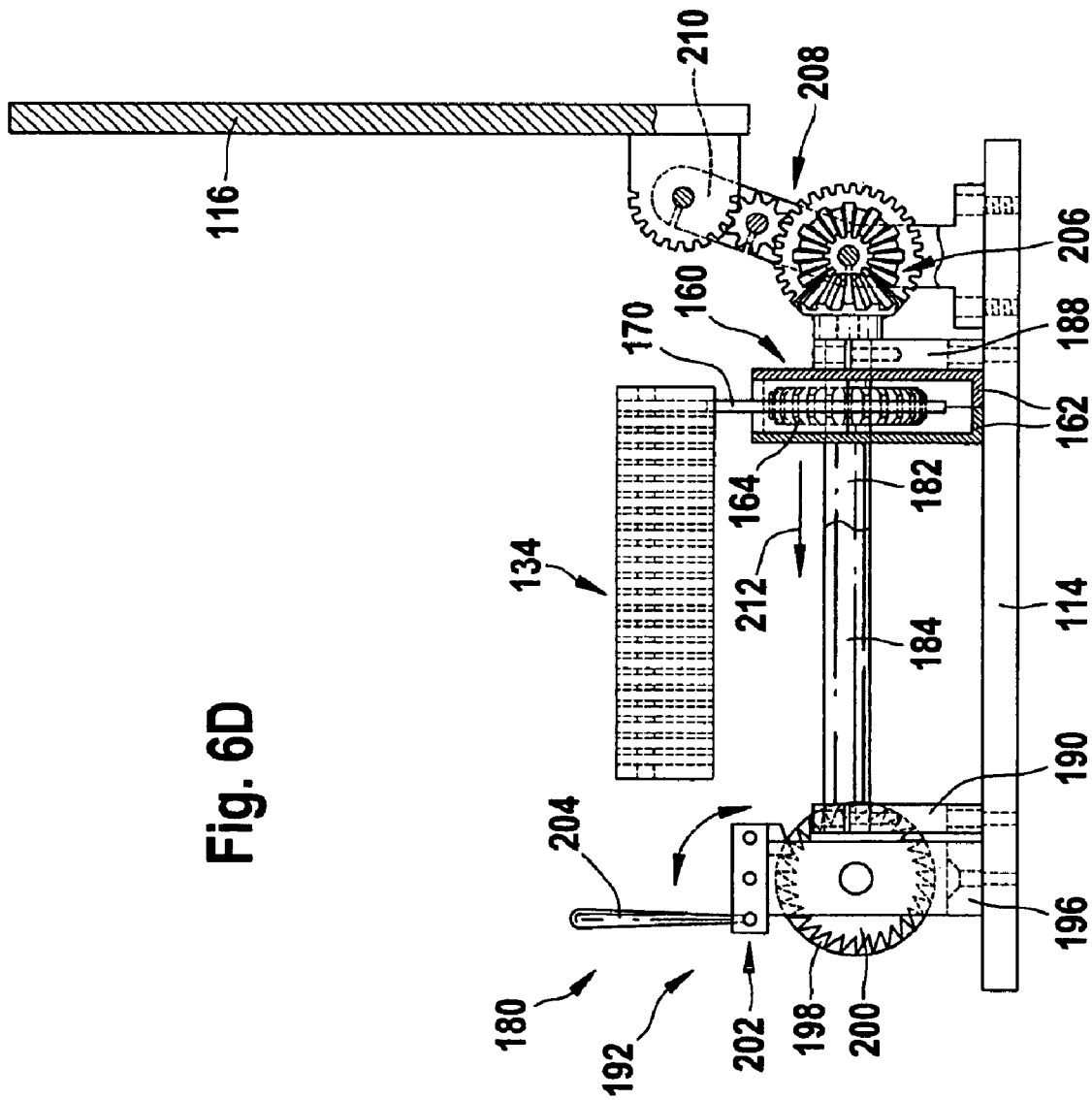

The drive shaft 182 is connected by an angular gear 206 to a toothed gear 208 of the lid 116 (see FIGS. 6C and 6D). The toothed gear 208 is in turn mounted on a lid holder 210, which is connected fixedly to the bottom part 114 of the housing, such that a folding-open movement of the lid 116, relative to the bottom part 114 of the housing is permitted. At the same time, the lid 116 is pretensioned relative to the bottom part 114 of the housing by a spring (not shown) in the direction of a folding-open movement. In the closed state of the housing 112 (FIGS. 6A and 6C), the lid 116 is secured by a lock (not shown), which thus prevents folding-open of the lid 116. It is only when the release button 124 is actuated that the lid 116 is freed and, driven by the spring force, can fold open. However, during the opening movement of the lid 116, the drive shaft 182 is rotated via the angular gear 206 and in turn drives the toothed wheel 164 of the dispensing device 160, as a result of which a test strip 136 is dispensed from the magazine 134 by the transport arm 166.

Overall, the general operation of dispensing a test strip 136 from the magazine 134 therefore involves the following steps. A user actuates the release button 124 of the housing 112. By way of the trigger lever 204 and the balance wheel 200, the dispensing device 160 is positioned onward by exactly one cavity 135. At the same time, by actuating the release button 124, the lid 116 is freed and, driven by spring force, folds open. The toothed wheel 164 of the dispensing device 160 is actuated via the drive shaft 182, as a result of which the dispensing device 160, by way of the transport arm 160, in turn conveys exactly one test strip 136 to the application and measurement position shown in FIG. 5E, such that a measurement can be performed.

The features disclosed in the above description, the claims and the drawings may be important both individually and in any combination with one another for implementing the present invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A test device for determining the concentration of at least one analyte in a sample, the device comprising:
a housing having a closed state and an opened state:
a storage device removably received within the housing, the storage device comprising a magazine having plurality of cavities, each cavity configured for receiving a substantially flat test strip in a storage position and in a substantially parallel orientation to test strips in a storage position in other cavities of the storage device;
a dispensing device configured to engage a test strip received within the storage device and to convey the test strip from the storage position to a measurement position during opening of the housing, the opening being effected when the housing is moved from the closed state to the opened state; and
a measuring device provided within the housing and configured to determine the concentration of the at least one analyte concentration in a sample when the sample is applied to a test strip which is moved to the measurement position, the measuring device operatively engaging the test strip when the test strip is conveyed to the measurement position.

2. The test device of claim 1, wherein the housing is configured to be in a folded configuration when in a closed state, the opening of the housing being effected when the housing is unfolded into an opened state.

3. The test device of claim 1, wherein the dispensing device comprises a rotation axle for effecting a rotational movement of the test strip from the storage position to the measurement position when the dispensing device engages the test strip within the storage device.

4. The test device of claim 1, wherein the storage device comprises at least one membrane covering at least one cavity of the storage device and configured to protect the test strip within the cavity from air, moisture and dirt, the membrane being perforatable by the test strip when the strip is conveyed from the storage position to the measurement position.

5. The test device of claim 1, wherein the storage device further comprises a desiccant configured to reduce moisture within the cavities of the storage device.

6. The test device of claim 5, wherein the desiccant is provided at or in one or more of the group consisting of at least one of the cavities, at least one test strip, and the magazine.

7. The test device of claim 1, wherein at least one measurement position has contacts for contacting the at least one test element.

8. The test device of claim 1, wherein the dispensing device is further configured to return a test strip from the measurement position to the storage position during re-closure of the housing.

9. The test device of claim 1, further comprising a selector device configured to locate the dispenser device in a position relative to the storage device in order to select an unused test strip for conveyance from its storage position to its measurement position upon the opening of the housing.

10. The test device of claim 1, further comprising a decoupling mechanism, said decoupling mechanism configured to be activated to prevent the dispensing device from conveying a test strip from to a measurement position during opening of the housing.

11. The test device of claim 1, wherein the measuring device is configured and arranged to carry out at least one of the measurements in the group consisting of: a glucose measurement, a cholesterol measurement, a coagulation measurement, and an immunology measurement.

12. A magazine for use in the test device of claim 1, the magazine comprising a plurality of stacked cavities each configured to receive a substantially flat test strip, each test strip being received parallel to one another in the cavities, wherein each test strip comprises at least one connecting device for connecting the test element to the dispensing device.

13. The magazine of claim 12, wherein the connecting device comprises at least one opening through each test strip for passage of a rotation axle.

14. The magazine of claim 12, wherein each test strip is configured for electrochemical determination of the at least one analyte concentration.

15. The magazine of claim 12, wherein each test strip comprises a capillary system for conveying a liquid sample from an application site to a measurement site.

* * * * *